United States Patent
Hopkins et al.

(10) Patent No.: US 7,556,414 B2
(45) Date of Patent: Jul. 7, 2009

(54) ENDOSCOPIC LIGHT SOURCE SAFETY AND CONTROL SYSTEM WITH OPTICAL SENSOR

(75) Inventors: Vernon Hopkins, Worcester, MA (US); Dana J. Landry, Sturbridge, MA (US); John P. Morahn, Willimantic, CT (US); Dashiell Birnkrant, Worchester, MA (US); Brad A. Picard, Foster, RI (US)

(73) Assignee: Karl Storz Endovision, Inc., Charlton, MA (US)

( * ) Notice: Subject to any disclaimer, the term of this patent is extended or adjusted under 35 U.S.C. 154(b) by 329 days.

(21) Appl. No.: 11/370,717

(22) Filed: Mar. 8, 2006

(65) Prior Publication Data

US 2007/0093690 A1 Apr. 26, 2007

Related U.S. Application Data

(63) Continuation-in-part of application No. 11/245,512, filed on Oct. 7, 2005.

(51) Int. Cl.
*A61B 1/06* (2006.01)

(52) U.S. Cl. ............... 362/574; 362/231; 362/804; 600/178; 600/181

(58) Field of Classification Search ........... 362/572, 362/574, 575, 231, 804; 600/160, 178, 179–182
See application file for complete search history.

(56) References Cited

U.S. PATENT DOCUMENTS 5,730,702 A    3/1998  Tanaka et al.  ............ 600/180
6,293,911 B1 *  9/2001  Imaizumi et al.  .......... 600/160
6,482,150 B2 * 11/2002  Utsui  ..................... 600/178
6,511,422 B1    1/2003  Chatenever  ............... 600/180
6,734,411 B1    5/2004  Imbsei et al.  ............ 250/205
6,932,809 B2 *  8/2005  Sinofsky  .................. 606/12
6,949,069 B2 *  9/2005  Farkas et al.  ............. 600/178
7,029,437 B2 *  4/2006  Kobayashi  ................ 600/180

(Continued)

FOREIGN PATENT DOCUMENTS

DE    199 47 812    5/2001

(Continued)

OTHER PUBLICATIONS

European Search Report, Nov. 29, 2007, 3 Pages.

*Primary Examiner*—Stephen F. Husar
*Assistant Examiner*—Peggy A. Neils
(74) *Attorney, Agent, or Firm*—St. Onge Steward Johnson & Reens LLC

(57) ABSTRACT

An endoscope light source safety system, including visible light transmitted along an illumination path, one or more sources for providing radiation along at least a portion of the illumination path, an optical element for combining the radiation from said one or more sources into the illumination path, an illumination attenuator connectable to the illumination path for receiving said visible light and the radiation, a reflector connected to said illumination attenuator for transmitting said visible light and returning at least a portion of the radiation, and one or more detectors for receiving the returned radiation from said reflector and for generating a signal indicative of the receipt of visible light by said illumination attenuator.

18 Claims, 8 Drawing Sheets

U.S. PATENT DOCUMENTS

| | | | |
|---|---|---|---|
| 7,077,804 B2 * | 7/2006 | Ota | 600/180 |
| 7,160,014 B2 * | 1/2007 | Sasaki et al. | 362/574 |
| 7,404,929 B2 * | 7/2008 | Fulghum, Jr. | 422/82.05 |
| 2003/0135205 A1 * | 7/2003 | Davenport et al. | 606/3 |
| 2005/0213984 A1 | 9/2005 | Liu | 398/139 |

FOREIGN PATENT DOCUMENTS

| | | |
|---|---|---|
| EP | 0 018 125 | 10/1980 |
| EP | 0 048 410 | 3/1982 |
| EP | 1 568 333 | 8/2005 |
| EP | 1772096 A2 | 4/2007 |

\* cited by examiner

ENDOSCOPIC LIGHT SOURCE SAFETY AND CONTROL SYSTEM WITH OPTICAL SENSOR

CROSS-REFERENCE TO RELATED APPLICATIONS

This application is a continuation in part of U.S. patent application Ser. No. 11/245,512 filed Oct. 7, 2005.

FIELD OF THE INVENTION

The invention relates to endoscopic systems, and more specifically to an endoscopic system having an optical detection means for determining the presence of an endoscope.

BACKGROUND OF THE INVENTION

Conventional endoscopes are often supplied with illumination from an external light source. Such light sources generally include high powered lamps, such as xenon lamps. The light sources are generally coupled to the endoscope by means of a detachable waveguide or fiber optic light cable.

An endoscope may be disconnected from the waveguide while still energized by the light source. Light exiting from the waveguide may therefore cause damage if the waveguide is set down without the medical instrument attached. For example, the light may damage operating drapes, a patient's skin, or clothing. Therefore, it is desirable that the light exiting the waveguide be attenuated when the endoscope is determined to be disconnected from the waveguide or fiber optic light cable.

Some devices exist to determine the presence of a light cable on a light source. For example, U.S. Pat. No. 4,356,534 to Hattori discloses a light supply device having a means for detecting a connection between a connector of a cable and a light supply socket using a relay switch operated by a solenoid. U.S. Pat. No. 4,433,675 to Konoshima discloses a light supply apparatus for an endoscope having a detecting section to detect the state of a coupling between a connector and a socket mounted on a housing of the light supply. However, Both Hattori and Konoshima disclose only means for detecting the presence of a connection between a connector and a socket of a light supply. Neither patent discloses a system for detecting the presence of an endoscope on a waveguide.

U.S. Pat. No. 6,110,107 to Bellahsene et al. discloses a fiber optic cable for supplying light to an endoscope and for detecting the presence of the endoscope. However, the specialized cable disclosed in Bellahsene requires electrical conductors running the length of the cable and a switch on the cable's end with a sensor configured to sense the proximity of the endoscope. Therefore, the teachings of Bellahsene may not be used to detect the presence of an endoscope in existing endoscopic systems without using the specialized cable.

It is therefore desired to provide an improved system and method for detecting the presence of an illumination attenuator, such as an endoscope, along an illumination path. It is a further desired to provide such a system that is adaptable to existing illumination attenuator systems without the necessity for a specialized cable or waveguide.

SUMMARY OF THE INVENTION

According, it is an object of the present invention to provide an endoscopic system having an optical detection means for determining the presence of an endoscope or any other illumination attenuator. It is a further object to provide the endoscopic system in which the system controls a light source providing illumination to the illumination attenuator (e.g., endoscope).

It is a further object of the present invention to provide an optical sensor for detecting the presence of an endoscope in an endoscopic system. It is a further object to provide the optical sensor is adaptable to existing endoscopic systems.

These and other objectives are achieved by providing an endoscope light source safety system, including visible light transmitted along an illumination path, one or more sources for providing radiation along at least a portion of the illumination path, an optical element for combining the radiation from said one or more sources into the illumination path, an illumination attenuator connectable to the illumination path for receiving said visible light and the radiation, a reflector connected to said illumination attenuator for transmitting said visible light and returning at least a portion of the radiation, and one or more detectors for receiving the returned radiation from said reflector and for generating a signal indicative of the receipt of visible light by said illumination attenuator.

Further provided is an endoscope light source safety system, including visible light transmitted along an illumination path, an array of sources, each source for providing radiation along at least a portion of the illumination path, an optical element for reflecting the radiation from the sources into the illumination path, an illumination attenuator connectable to the illumination path for receiving said visible light and returning at least a portion of the radiation to said optical element, and an array of detectors, at least one of the detectors receiving via said optical element a portion of the returned radiation and generating a signal indicative of the receipt of visible light by said illumination attenuator.

DETAILED DESCRIPTION OF THE INVENTION

Figure 1:
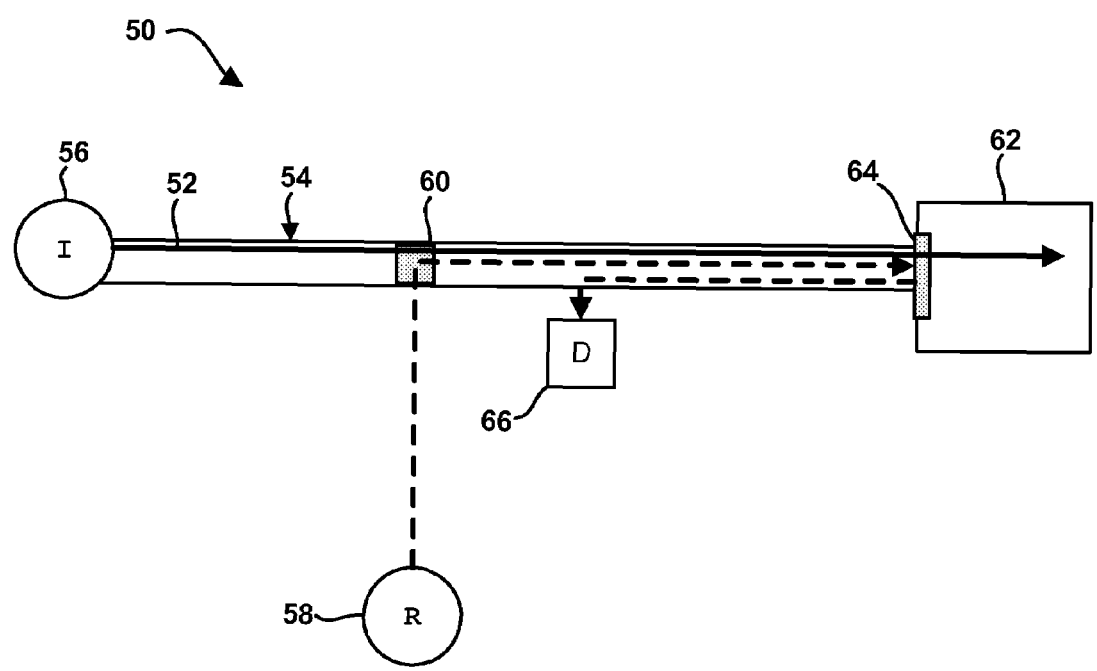
FIG. 1 is a schematic diagram of an endoscopic system according to the present invention.

FIG. 1 shows a schematic of an endoscopic system 50 according to the present invention. The system 50 includes visible light 52 being transmitted along an illumination path 54. In some embodiments, the visible light 52 may originate from an illuminator 56. The system 50 also includes a source 58 for providing radiation along at least a portion of the illumination path 54. The radiation may be combined into the illumination path 54 via a combiner 60.

Further included in the system 50 is an illumination attenuator 62. The illumination attenuator 62 may be any device for receiving visible light. Preferably, the illumination attenuator 62 is a device being capable of also transmitting or projecting a portion of the visible light. For example, the illumination attenuator 62 may be an endoscope or a similar surgical instrument.

The system 50 includes a reflector (e.g., first reflector 64) connected to the illumination attenuator 62 for reflecting at least a portion of the radiation received by the illumination attenuator 62 (e.g., endoscope). The first reflector 64 may be mounted within the illumination attenuator 62 or external to the illumination attenuator 62. In some embodiments, the first reflector 64 is in the illumination path 54 and transmits at least a portion of visible light received by the illumination attenuator 62.

A detector 66 is included in the system 50. The detector 66 may receive a portion of radiation reflected from the first reflector 64. In some embodiments, the portion is reflected from the combiner 60 to the detector 66. The detector 66 may further generate a signal (not shown) indicative of the receipt of visible light 52 by the illumination attenuator 62. In some embodiments, the signal is provided to control the amount of visible light provided by an illuminator (e.g., illuminator 56).

Figure 2:
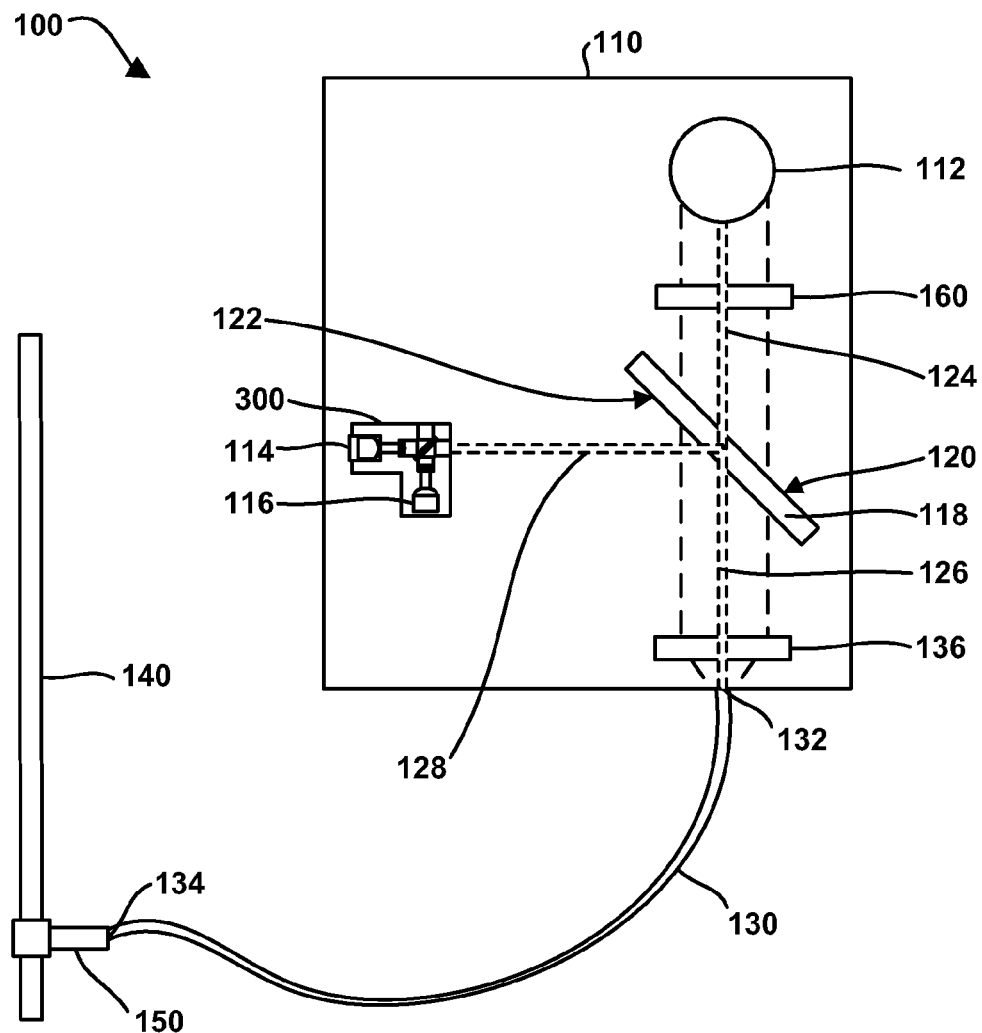
FIG. 2 is another schematic diagram of an endoscopic system according to the present invention.

FIG. 2 shows a schematic of an exemplary embodiment of an endoscopic system 100 according to the present invention. The system 100 includes an illumination supply device 110. The illumination supply device 110 includes an illuminator 112 for providing visible light (e.g., visible light 52). The visible light may be provided at a first frequency or a first frequency range (e.g., within the visible range of the electromagnetic spectrum). The illuminator 112 may be any known illuminator, such as a xenon lamp.

The illumination supply device 110 further includes a source 114 for providing radiation (e.g., detection radiation) at a second frequency or second frequency range. In a preferred embodiment, the second frequency range is less than the first frequency range (e.g., infrared radiation frequencies and visible light frequencies, respectively). For example, the source 114 may be an IR light emitting diode ("LED") providing infrared ("IR") radiation. In other embodiments, the second frequency range may be greater than the first frequency range (e.g., ultraviolet radiation frequencies and visible light frequencies, respectively). The source 114 may provide constant radiation or modulated radiation, i.e., at a particular pulse rate. For example, the source 114 may provide radiation pulsed at 455 kHz with a 4.2 kHz envelope. The source 114 may further provide radiation pulsed at 31-38 kHz with an 8-bit data stream (e.g., "10100110").

The illumination supply device 110 of the endoscopic system 100 further includes a detector 116 (e.g., IR receiving module). The detector 116 may generate a signal upon the receipt or detection of particular radiation or light. For example, the detector 116 may generate a signal upon the receipt of a specific frequencies or levels of radiation being reflected from a reflector and/or illuminator attenuator or endoscope.

In some embodiments, the detector 116 may generate a signal when radiation pulsed at a particular pulse rate is received. For example, the detector 116 may only detect radiation being pulsed at a rate of 455 kHz within a 1-22.5 kHz envelope or 950 nm. Such limits on detection and signal generation are desirable to prevent interferants from being detected, such as fluorescent light, incandescent lights, sun light or the visible light (e.g., 52). The detector 116 may further include built-in electronics such as a demodulator, gain control and/or data coder/decoder (not shown).

As shown in FIG. 2, the endoscopic system 100 may include a waveguide 130 detachably connectable to the illumination supply device 110 (e.g., via a waveguide socket (not shown)). The waveguide 130 includes a proximal end 132 and a distal end 134. The waveguide 130 may be any waveguide or light cable for providing an illumination path, such as a fiber optic cable. The endoscopic system 100 further includes an illumination attenuator 140 (e.g., an endoscope) being connectable to the illumination supply device 110 via the waveguide 130. For example, the illuminator attenuator 140 may include a waveguide fitting 150 (e.g., a light post connector) detachably connected to the distal end 134 of the waveguide 130.

Figure 3:
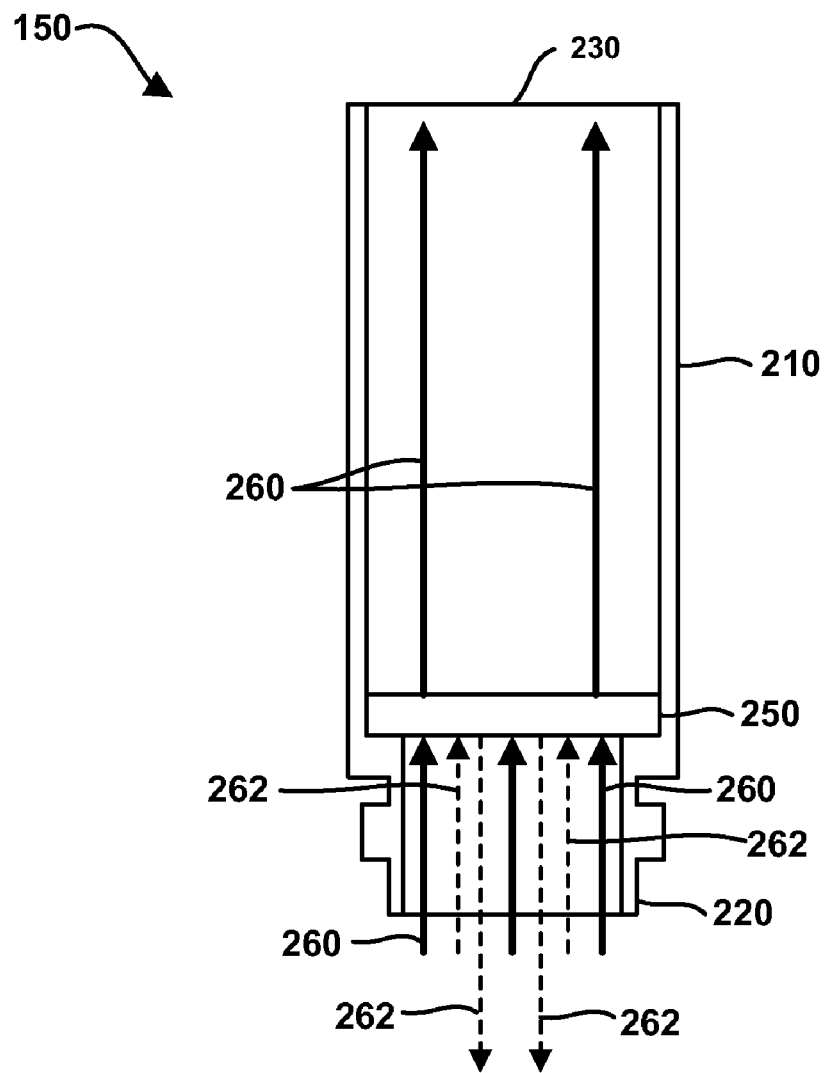
FIG. 3 is a cross sectional view of a waveguide fitting portion of the endoscopic system.

A cross sectional view of the waveguide fitting 150 or waveguide fitting adapter is shown in FIG. 3. The waveguide fitting 150 includes a housing 210 having a first end 220 and a second end 230. The first end 220 includes a means to detachably connect the waveguide fitting 150 to the waveguide 130. The second end 230 includes a means to detachably connect to the illuminator attenuator 140 (e.g., endoscope). In some embodiments, the second end 230 may be disconnected from the illuminator attenuator 140 only after the first end 220 is disconnected from the waveguide 130. Some embodiments of the waveguide fitting 150 may be adaptable to several known illumination attenuators (e.g., endoscopes) and waveguides. Therefore, the present invention may be readily implemented with (e.g., interchangeable between) existing endoscopic instruments, waveguides, and illumination supply devices.

The waveguide fitting 150 includes a first reflector 250. In one embodiment, the first reflector 250 may be, e.g., a "hot mirror" for transmitting the visible light and reflecting other light or radiation (e.g., radiation 260). The first reflector 250 may receive both visible light 260 and radiation 262 from the illumination supply device 110 via the waveguide 130. The first reflector 250 transmits a substantial portion of visible light 260 via the illuminator attenuator 140. The first reflector 250 reflects a substantial portion of radiation 262 to the detector 116 via the waveguide 130. As explained in more detail below, the presence of the illumination attenuator 140 may therefore be determined by detecting (via detector 116) whether radiation is reflected (i.e., an illumination attenuator 140 is attached) or not reflected (i.e., the illumination attenuator 140 is detached).

In other embodiments, the first reflector 250 may include, e.g., a cold filter. As one of ordinary skill in the art will understand, a cold filter may be employed to reflect shorter wavelengths of light or radiation and transmit longer wavelengths. For example, a cold filter may be used when the radiation has a higher frequency than the visible light. In some other embodiments, the first reflector 250 may include a notch filter to reflect one or more narrow bands of radiation or light and transmit wider regions of radiation around the rejected band(s).

The first reflector 250 may further include a unique indicator (not shown). Such indicator may provide information (e.g., parameters) from the illuminator attenuator 140 to the illumination supply device 110 via the reflected radiation 264. The parameters may be stored in the indicator or provided to the indicator by a user via a remote control (not shown) on the illuminator attenuator 140. The parameters may include, for example, an illumination attenuator or endoscope type, serial number, maximum temperature, a maximum light level input, and/or the remote controls present. For example, the indicator may include an integrated circuit providing parameters (e.g., instructions) to the illumination supply device 110, such as to adjust the intensity of the illuminator 112 in real time. The indicator may further be powered using light from the illumination supply device 110.

As shown in FIG. 2, the illumination supply device 110 may further include an optical element 118 (e.g., a "hot mirror" and/or a second reflector). The optical element 118 includes a first surface 120 and a second surface 122. The optical element 118 is positioned to receive visible light from the illuminator 112 via the first surface 120, and reflect radiation from (e.g., and to) the source 114 via the second surface 122. For example, the optical element 118 may be positioned at approximately a forty-five degree angle relative to a first portion 124 (from the illuminator 112) and approximately a forty-five degree angle relative to a radiation path 128 (from the source 114). In the exemplary embodiment, the first portion 124 is oriented ninety degrees relative to the radiation path 128.

As one of ordinary skill in the art will understand, the optical element 118 of the present embodiment may be implemented in conventional illumination supply devices, in part, by removing a current zero degree mirror and replacing it with the above described forty-five degree hot mirror. The orientation of the optical element 118 in the present invention allows for the rejection of radiation from the lamp (e.g., illuminator 112), but further creates a radiation path for the transmission of radiation to and from the detector 116.

As shown in FIG. 2, the optical element 118 may receive visible light from the illuminator 112 via a first portion 124 of an illumination path and transmit the visible light to the waveguide 130 (i.e., combined into the illumination path) via a second portion 126 (e.g., via a lens 136). The optical element 118 may further receive radiation (from the source 114) via a radiation path 128 and reflect the radiation to the waveguide 130 via the second portion 126. If the illuminator attenuator 140 is present (i.e., connected to the waveguide 130), the radiation, or a substantial portion thereof, will be reflected from the first reflector 250 and returned via the waveguide 130 and second portion 126. The optical element 118 may receive the reflected radiation via the second light 126 path and reflect the radiation to the detector 116 via the radiation path 128 (i.e., diverted from the illumination path).

If the illuminator attenuator 140 is not present, little or no radiation will be returned via the waveguide 130 or received by the detector 116. The illuminator 112 may be controlled (e.g., powered down or turned off) depending on the radiation received. For example, the illuminator 113 may provide visible light only while the detector 116 receives at least a predetermined amount or level of the radiation (e.g., radiation having the second frequency and/or radiation modulated at the particular pulse rate). The illuminator 112 may further not provide visible light when the detector 116 receives less than the predetermined amount of radiation.

Shown in FIG. 2, the illumination supply device 110 may include an iris 160 for controlling the illuminator 112. For example, the iris 160 may block visible light, or any portion thereof, being provided by the illuminator 112. The iris 160 may be positioned along the first portion 124. As one of ordinary skill in the art will understand, such placement of the iris 160 will allow for the control of visible light without interrupting the transmission and/or reflection of the radiation. The iris 160 may (e.g., upon receiving information from the detector 116) block a substantial portion of the visible light when the detector 116 does not receive radiation within a specific frequency range (e.g., a detection frequency range) and/or particular pulse rate (e.g., repetition rate), or coded data.

Figure 4:
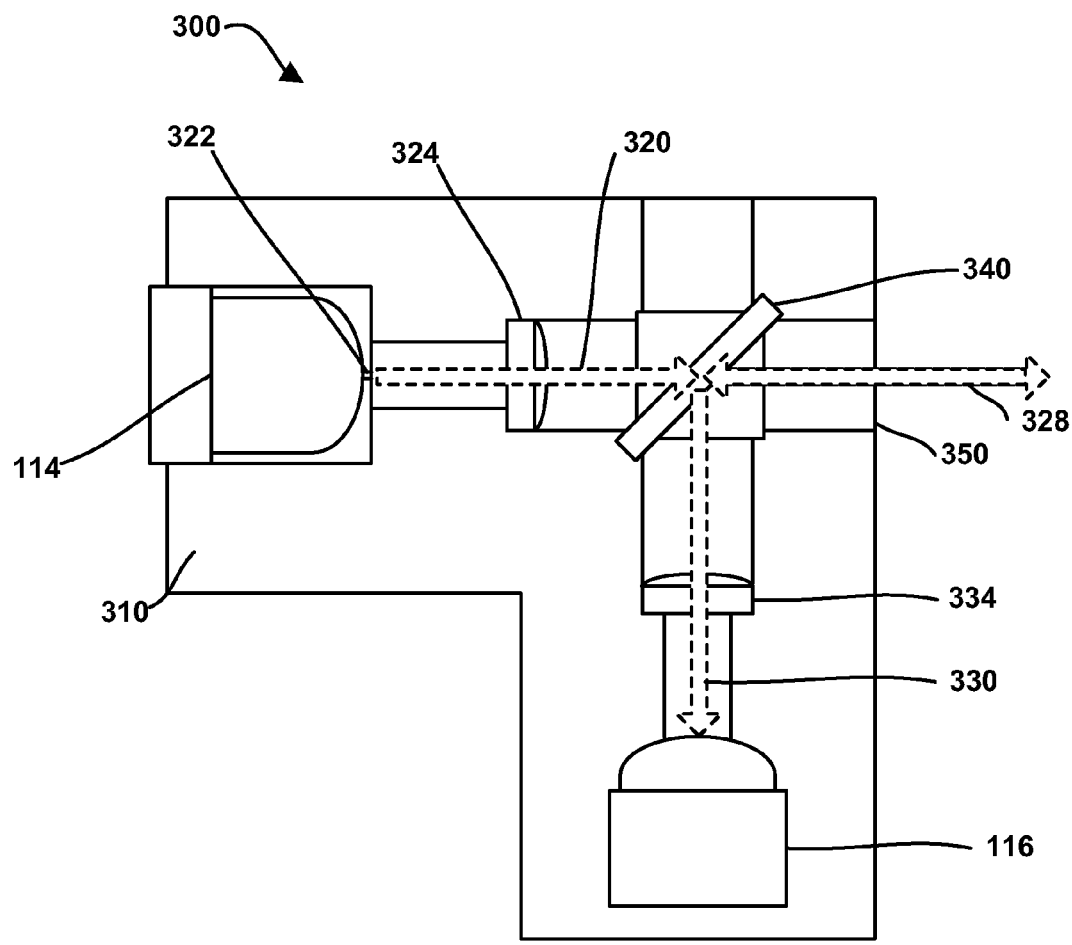
FIG. 4 is a schematic diagram of an optical sensor portion of the endoscopic system shown in FIG. 2.

In some embodiments of the present invention, the source 114 and the detector 116, described above, may be integrated in an optical sensor 300. FIG. 4 shows a schematic diagram of one optical sensor 300 for detecting the presence of an endoscope according to the present invention.

The optical sensor 300 includes a housing 310 and the source 114 (e.g., an infrared radiation source). The source 114 provides radiation along a source path 320. The source 114 may include a field stop 322 (e.g., 0.25 mm pinhole). Further included may be a collimating lens 324 positioned along the source path 320. The optical sensor 300 further includes the detector 116 for receiving reflected radiation via a detection path 330. A focusing lens 334 may be included along the detection path 330.

Shown in FIG. 4, the optical sensor 300 includes a sensor reflector 340. The sensor reflector 340 may be any reflector and/or filter for allowing a portion of received radiation to pass through while reflecting another portion. For example, the sensor reflector 340 may be a 50/50 infrared beam splitter. The sensor reflector 340 receives the radiation (e.g., provided at a specific detection frequency or range of detection frequencies) via the source path 320 and transmits the radiation to the illumination attenuator 140 via an output/return port 350 and the radiation path 328. The sensor reflector 340 may further receive reflected radiation, i.e., reflected from the first reflector 250 of the illumination attenuator 140, via the radiation path 328. The sensor reflector 340 then transmits a portion of reflected radiation to the detector 116 via the detection path 330.

The optical sensor 300 may positively detect the presence of the illumination attenuator or endoscopic device 140 (i.e., attached to the waveguide 140) when the detector 116 receives reflected radiation within the detection frequency range (and/or a particular pulse rate). The detector 116 may then provide information to the system 100 to adjust or control the illuminator 112 as needed. The optic sensor 300 may detect the presence of the endoscopic device 140 at given time intervals, continuously, and/or upon command by the system 100. The optical sensor 300 is preferably small enough to fit in existing illumination supply devices. For example, one embodiment of the optical sensor 300 may include the following approximate dimensions: 26 mm height, 24 mm width, and 14 mm thickness.

Figure 5:
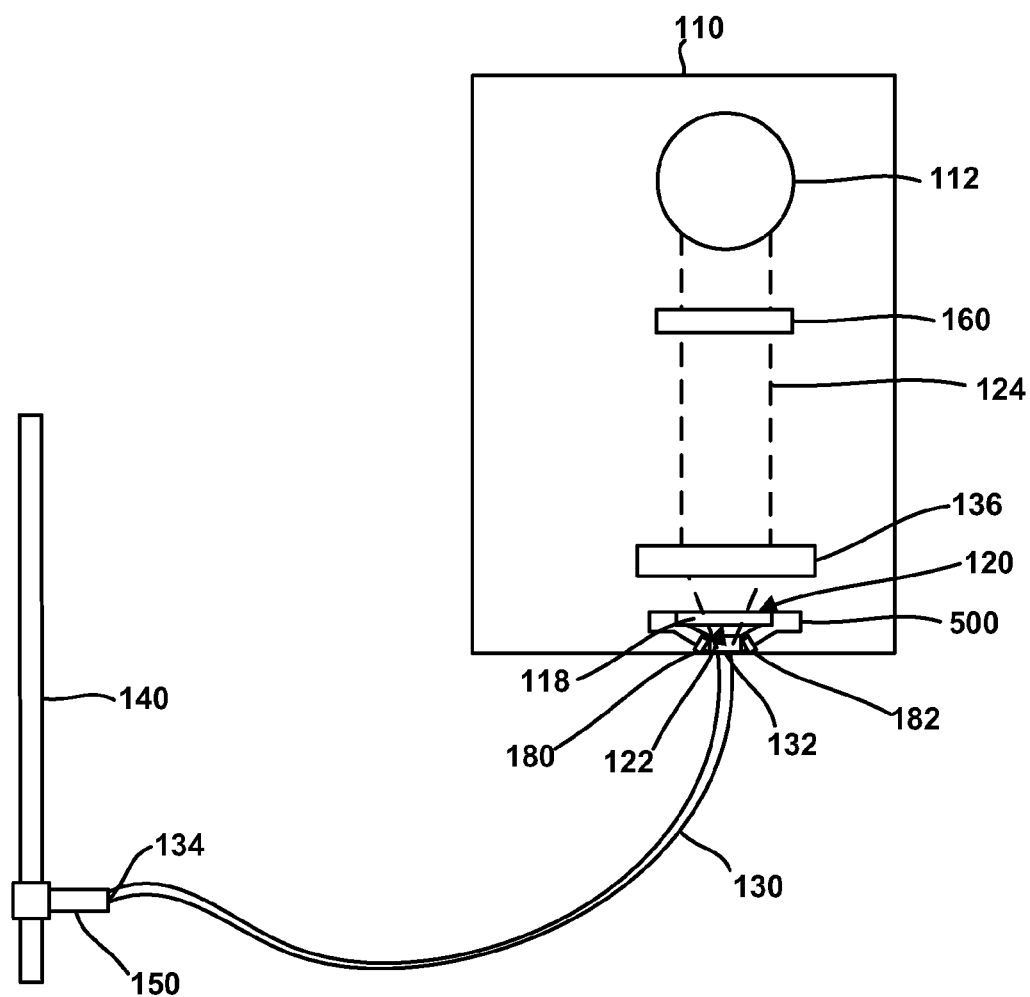
FIG. 5 is another schematic diagram of an endoscopic system according to the present invention.

FIG. 5 shows another embodiment of the system according the present invention. The present embodiment includes the illumination supply device 110 having an illuminator 112 for providing illumination or visible light along an illumination path 124. The present embodiment may further include a lens 136 and iris 160.

The system shown in FIG. 5 also includes an optical element 118 have a first surface 120 and a second surface 122. The optical element 118 may be housed in an optical sensor 500 (shown in FIGS. 6A-6C). As in the previously described embodiment, the optical element 118 receives visible light from the illuminator 112 via the first surface 120 and reflected radiation via the second surface 122. The optical element 118 further transmits visible light and detection radiation via the waveguide 130.

The system of FIG. 5 further includes at least one source 180 for providing detection radiation (e.g., infrared radiation) and at least one detector 182 for receiving detection radiation. Each source 180 and detector 182 is mounted in a housing 502 of the optical sensor 500. Further, a source 180 and detector 182 may further be collocated in a single sub-housing.

Figure 6A:
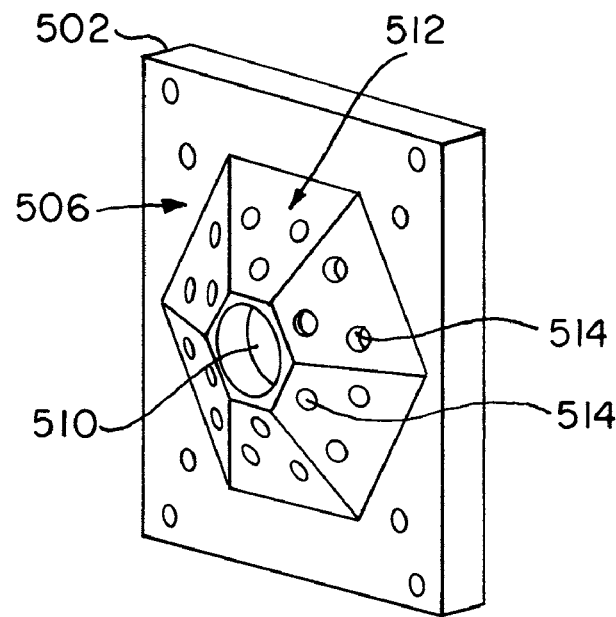
FIG. 6A is a schematic diagram of an optical sensor housing of the endoscopic system shown in FIG. 5.
Figure 6B:
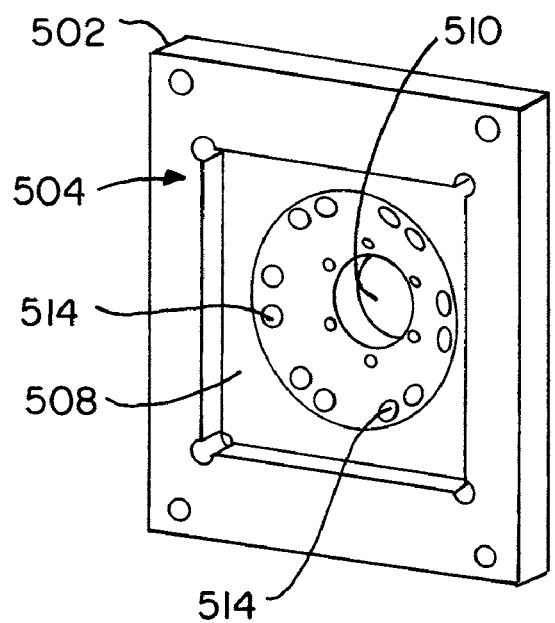
FIG. 6B is another schematic diagram of the optical sensor housing the endoscopic system shown in FIG. 5.
Figure 6C:
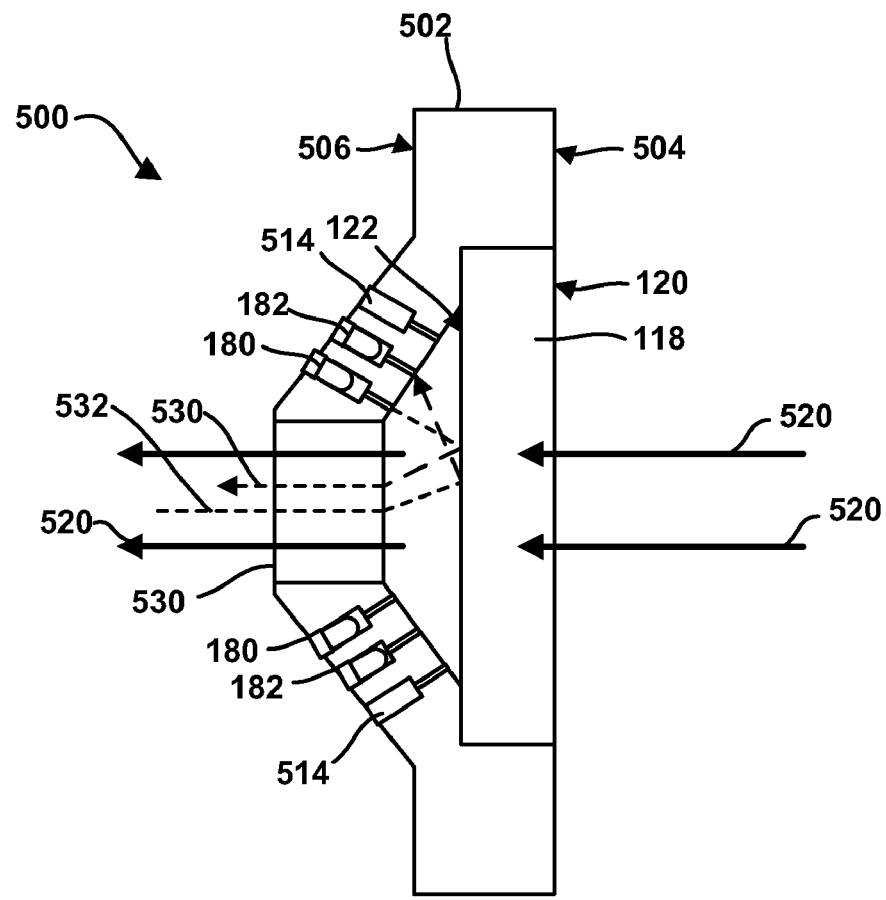
FIG. 6C is a cross sectional view of an optical sensor portion of the endoscopic system shown in FIG. 5.

FIGS. 6A-6C show the optical sensor 500 according to the present invention. In particular, FIGS. 6A-6B show the housing 502 of the optical sensor 500. The housing 502 may be manufactured from any known material, e.g., metal or plastic. For example, the housing 502 may be manufactured from polyetheretherketone or "PEEK." The housing may be any size depending on the particular endoscopic system and/or illumination supply device it is used with. In one embodiment, the housing 502 is approximately 36 mm×40 mm×10 mm.

The housing 502 includes a first side 504 and a second side 506. The first side 504 includes a portion 508 for receiving and/or mounting the optical element 118. The housing 502 further includes an illumination channel 510 or aperture (e.g., approximately 8 mm in diameter) for passing the visible light or illumination to/from the waveguide 130. The housing 502 further includes a radial portion 512 having any number of radial channels 514 or apertures (e.g., approximately 2 mm in diameter) for housing sources 180 and detectors 182.

The radial channels 514 and/or radial portion 512 may be angled to provide for the transmission of detection radiation to and from the illumination channel 510 via the second surface 122 of the optical element 118. For example, some radial channels 501 may be angled approximately 30 degrees from an axis of the illumination channel 510. As one of ordinary skill in the art will understand, the angle may be more for radial channels 514 located farther outboard of the illumination channel 510. Further, the radial channels 514 housing detectors 182 are positioned such that they receive/detect only radiation reflected from the illumination channel 510. Therefore, the optical sensor 500 will not provide a false reading of detection due to stray radiation received directly from a source 180 of the optical sensor 500.

Shown in FIG. 6C, the optical sensor 500 receives visible light 520 (e.g., from the illuminator 112) via the first surface 120 of the optical element 118. The optical element 118 may transmit the visible light 520 via the illumination channel 510 and to the waveguide 130. One or more sources 180 may also transmit detection radiation 530 to the waveguide 130. As shown, each source 180 is positioned such that detected radiation transmitted therefrom will reflect off the optical element 118 and to the waveguide (via the illumination channel 510). The visible light 520 and detection radiation 530 may then be received by the illumination attenuator 140 or waveguide fitting 150 thereof.

As described above, a substantial portion of the visible light 520 may pass to the illumination attenuator 140 if an illumination attenuator 140 is attached or present. If the illuminator attenuator 140 is present (i.e., connected to the waveguide 130), detection radiation will be reflected from the waveguide fitting 150 and/or first reflector 250 and returned via the waveguide 130. The optical element 118 may receive the reflected radiation 532 and reflect the radiation 532 to any one or all of the detectors 182 in the optical sensor 500. One or more detectors 182 may then generate a signal indicating that the illuminator 112 may remain on and/or the iris 160 remain open. If the illuminator attenuator 140 is not present, little or no radiation 532 will be returned via the waveguide 130 or received by the detectors 182. The detectors 182 may then generate a signal indicating to the system to shut off the illuminator 112 and/or close the iris 160. In some embodiments, the lack of signal from a detector 182 similarly indicates to the system to shut off the illuminator 112 and/or close the iris 160.

Figure 7:
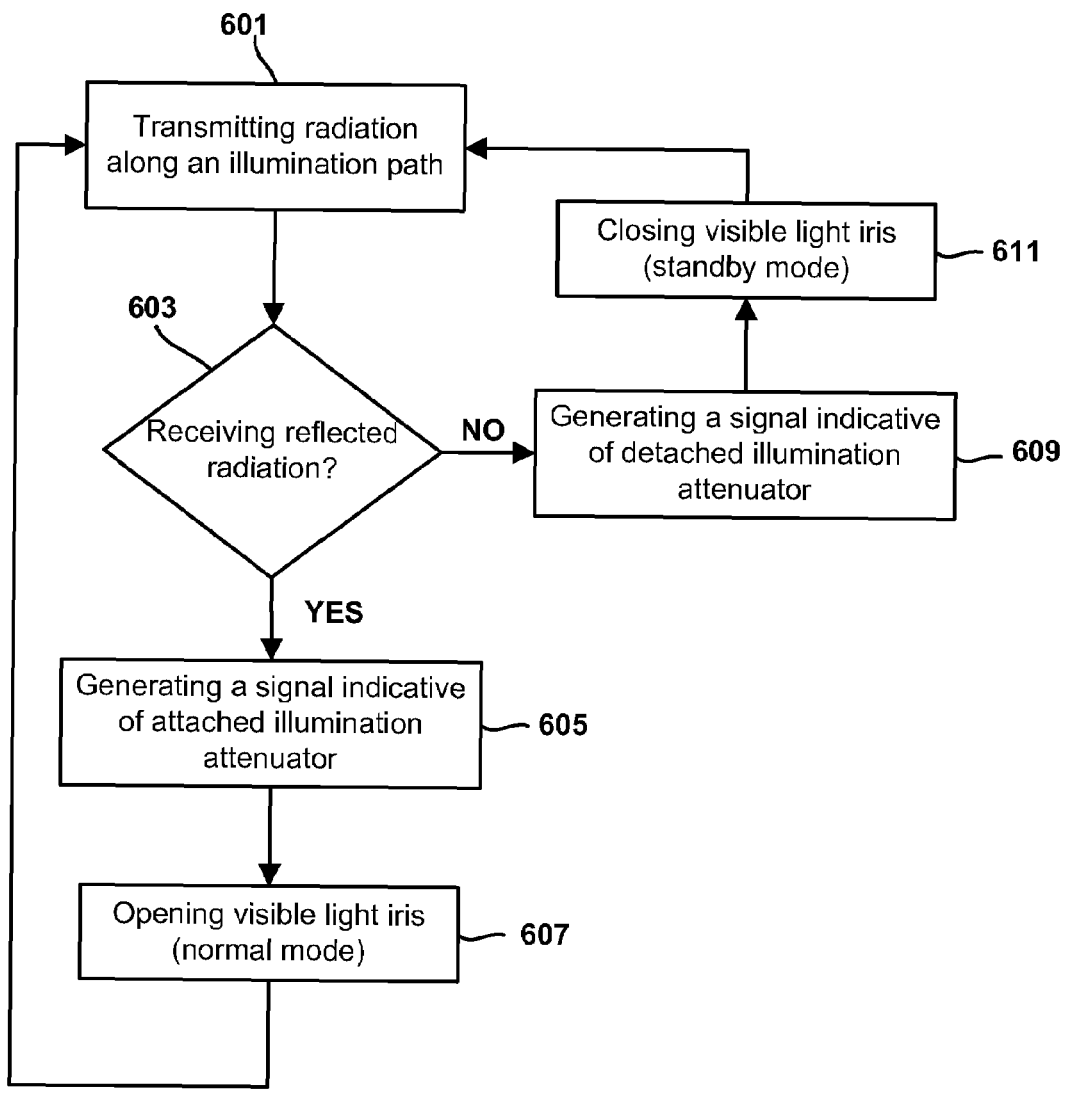
FIG. 7 is a method for controlling an endoscope light source employable by the systems shown in FIGS. 1-6C.

FIG. 7 shows a method for controlling an endoscope light source according to the present invention. The method is described with respect to the systems shown in FIGS. 1-6C. However, one of ordinary skill in the art will understand that the method may be implemented in other systems and devices. The method includes a step 601 of transmitting radiation (e.g., infrared radiation and/or detection radiation) along an illumination path. The radiation may, e.g., be transmitted at a detection frequency (and/or a pulse rate) or coded data to an endoscope via a waveguide. Step 603 includes detecting (e.g., via detector 116/182) the receipt of reflected radiation from the illumination path, e.g., being reflected from the first reflector 250 via the waveguide 130. If reflected radiation is received (e.g., by detector 116/182), a signal is generated that is indicative of an illumination attenuator being present and/or connected along the illumination path (step 605). The iris 160 may then be opened (or may remain open) allowing the illuminator 112 to transmit visible light (step 607). If the radiation is not received, a signal is generated that is indicative of an illumination attenuator not being present and/or being detached from the waveguide (step 609). The iris 160 may then be closed (or may remain closed) preventing the illuminator 112 from transmitting visible light (step 611).

Advantages of the present invention include the provision of a system and method for accurately detecting the presence of an illuminator attenuator or endoscope using radiation. Furthermore, the present invention provides a system and method to in which no electrical conductors need be connected to the endoscope to detect its presence. The electronics of the detection system may be contained within the illumination supply device and therefore no custom waveguide or fiber optic cable is required.

A further advantage of the present invention is the provision of an optical detection system by which parameters of an endoscope or information may be provided to the illumination supply device via radiation.

A further advantage of the present invention is the provision of the system and method being adaptable to existing endoscopic systems and components. It is contemplated that the present invention may be implemented in many existing illumination supply devices.

Although the invention has been described with reference to a particular arrangement of parts, features and the like, these are not intended to exhaust all possible arrangements or features, and indeed many modifications and variations will be ascertainable to those of skill in the art.

What is claimed is:

1. An endoscope light source safety system, comprising:
   visible light transmitted along an illumination path, said visible light having a first frequency;
   a housing having a first aperture for passing visible light and a plurality of second apertures circumscribing the first aperture;
   one or more sources for providing radiation via at least one second aperture along at least a portion of the illumination path, the radiation having a second frequency different from the first frequency;
   an illuminator attenuator connectable to the illumination path for receiving said visible light and the radiation;
   an optical element for combining the radiation from said one or more sources into the illumination path, receiving returned radiation from the illumination attenuator and transmitting at least a portion of the returned radiation to at least one of the detectors;
   a reflector connected to said illumination attenuator for transmitting said visible light and returning at least a portion of the radiation; and
   two or more detectors for receiving the returned radiation from the illumination path via said reflector and for generating a signal indicative of the receipt of visible light by said illumination attenuator.

2. The system according to claim 1, wherein the housing includes said optical element.

3. The system according to claim 1, wherein said housing circumscribes a portion of the illumination path.

4. The system according to claim 1, further comprising:
an illuminator for transmitting said visible light,
wherein the signal is provided for controlling said illuminator.

5. An endoscope light source safety system, comprising:
a housing having a first aperture and a plurality of second apertures circumscribing the first aperture;
visible light transmitted through the first aperture and along an illumination path, said visible light having a first frequency;
an array of sources arranged about the illumination path in the second apertures, each source for providing radiation via at least one of the second apertures and along at least a portion of the illumination path, the radiation having a second frequency different from the first frequency;
an optical element for reflecting the radiation from the sources into the illumination path;
an illumination attenuator connectable to the illumination path for receiving said visible light and returning at least a portion of the radiation to said optical element;
an array of detectors arranged about the illumination path, at least one of the detectors receiving a portion of the returned radiation from the illumination path via said optical element and generating a signal indicative of the receipt of visible light by said illumination attenuator; and
wherein said optical element receives the returned radiation from the illumination attenuator and transmits at least a portion of the returned radiation to at least one of the detectors.

6. The system according to claim 5, wherein said optical element further passes the visible light.

7. The system according to claim 5, further comprising:
a housing, wherein said housing includes said array of sources and said array of detectors.

8. The system according to claim 7, wherein said housing further includes the optical element.

9. The system according to claim 5, wherein the illumination path includes a waveguide.

10. The system according to claim 5, wherein said illumination attenuator is an endoscope.

11. An optical sensor for detecting the presence of an illumination attenuator comprising:
a housing having a first aperture for passing visible light and a plurality of second apertures circumscribing the first aperture;
at least one source for providing radiation via at least one second aperture to an illumination path;
two or more detectors, each detector for receiving reflected radiation from the illumination path via at least one second aperture; and
an optical element for:
transmitting the visible light via the first aperture to an illumination attenuator,
receiving the radiation from the at least one source and transmitting at least a portion of the radiation along the illumination path to the illumination attenuator,
receiving returned radiation from the illumination attenuator, and
transmitting at least a portion of the returned radiation to at least one of the detectors,
wherein a signal indicative of the presence of the illumination attenuator is generated when at least one of the detectors receives returned radiation.

12. The optical sensor according to claim 11, the first aperture further for receiving a waveguide.

13. The optical sensor according to claim 11, wherein at least one of the second apertures has an axis oriented about thirty degrees to an axis of the first aperture.

14. The optical sensor according to claim 11, wherein said optical element includes a first surface and a second surface.

15. The optical sensor according to claim 14, wherein said optical element receives the visible light incident on the first surface and transmits the visible light via the second surface.

16. The optical sensor according to claim 15, the visible light being incident substantially normal to the first surface.

17. The optical sensor according to claim 14, wherein said optical element receives the radiation via the second surface and reflects the radiation via the second surface.

18. The optical sensor according to claim 17, the radiation being incident approximately 30 degrees from a normal to the second surface.

* * * * *